(12) United States Patent
Saito

(10) Patent No.: US 9,918,631 B2
(45) Date of Patent: Mar. 20, 2018

(54) ADAPTIVE OPTICAL APPARATUS AND OPHTHALMIC APPARATUS

(71) Applicant: CANON KABUSHIKI KAISHA, Tokyo (JP)

(72) Inventor: Kenichi Saito, Pittsford, NY (US)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/425,371

(22) PCT Filed: Oct. 18, 2013

(86) PCT No.: PCT/JP2013/078887
§ 371 (c)(1),
(2) Date: Mar. 3, 2015

(87) PCT Pub. No.: WO2014/073390
PCT Pub. Date: May 15, 2014

(65) Prior Publication Data
US 2015/0230704 A1     Aug. 20, 2015

(30) Foreign Application Priority Data

Nov. 9, 2012   (JP) .................. 2012-247747

(51) Int. Cl.
*A61B 3/14*     (2006.01)
*G02B 26/10*    (2006.01)
(Continued)

(52) U.S. Cl.
CPC ............. *A61B 3/14* (2013.01); *A61B 3/1015* (2013.01); *A61B 3/1025* (2013.01); *A61B 3/12* (2013.01);
(Continued)

(58) Field of Classification Search
CPC .. G02B 27/0068; A61B 3/1025; A61B 3/1015
(Continued)

(56) References Cited

U.S. PATENT DOCUMENTS 6,331,059 B1 * 12/2001 Kudryashov .......... A61B 3/103
351/221
6,890,076 B2   5/2005 Roorda
(Continued)

FOREIGN PATENT DOCUMENTS

CN     101862178 A    10/2010
CN     102038490 A     5/2011
(Continued)

OTHER PUBLICATIONS

Jan. 24, 2014 International Search Report and Written Opinion in International Patent Appln. No. PCT/JP2013/078887.
(Continued)

*Primary Examiner* — James Greece
*Assistant Examiner* — Travis Fissel
(74) *Attorney, Agent, or Firm* — Fitzpatrick, Cella, Harper & Scinto

(57) ABSTRACT

An adaptive optical apparatus includes a wavefront correction unit configured to correct a wavefront aberration, a first scanning unit configured to be arranged to be optically almost conjugate to the wavefront correction unit, and scan light on an object in a first direction, a second scanning unit configured to be arranged to be optically almost conjugate to the wavefront correction unit, and scan light on the object in a second direction perpendicular to the first direction, and an optical element arranged in an optical path between the wavefront correction unit and the first scanning unit and arranged in an optical path between the first scanning unit and the second scanning unit.

12 Claims, 15 Drawing Sheets

(51) Int. Cl.
*G02B 27/00* (2006.01)
*A61B 3/10* (2006.01)
*A61B 3/12* (2006.01)

(52) U.S. Cl.
CPC ....... *G02B 26/101* (2013.01); *G02B 27/0031* (2013.01); *G02B 27/0068* (2013.01)

(58) Field of Classification Search
USPC .............. 351/200, 208, 206, 246, 220, 243
See application file for complete search history.

(56) References Cited

U.S. PATENT DOCUMENTS

| | | | |
|---|---|---|---|
| 7,118,216 | B2 | 10/2006 | Roorda |
| 7,639,369 | B2* | 12/2009 | Owner-Petersen .... A61B 3/156 351/211 |
| 8,506,082 | B2 | 8/2013 | Saito |
| 8,699,015 | B2 | 4/2014 | Saito et al. |
| 8,902,432 | B2 | 12/2014 | Hirose et al. |
| 2003/0053026 | A1 | 3/2003 | Roorda |
| 2005/0174535 | A1* | 8/2005 | Lai ...................... A61B 3/1015 351/205 |
| 2006/0087617 | A1* | 4/2006 | Roorda .................... G01J 9/00 351/221 |
| 2007/0078308 | A1* | 4/2007 | Daly ...................... A61B 3/117 600/310 |
| 2007/0291230 | A1* | 12/2007 | Yamaguchi .......... A61B 3/1015 351/221 |
| 2011/0001930 | A1 | 1/2011 | Levecq |
| 2011/0096337 | A1 | 4/2011 | Hirose et al. |
| 2011/0234978 | A1* | 9/2011 | Hammer ................ A61B 3/102 351/208 |
| 2011/0242487 | A1 | 10/2011 | Yuasa et al. |
| 2011/0279778 | A1 | 11/2011 | Saito |
| 2012/0274904 | A1 | 11/2012 | Saito et al. |
| 2013/0021576 | A1 | 1/2013 | Saito |
| 2014/0055748 | A1 | 2/2014 | Saito |
| 2014/0160435 | A1 | 6/2014 | Saito |
| 2015/0131052 | A1 | 5/2015 | Saito et al. |

FOREIGN PATENT DOCUMENTS

| | | |
|---|---|---|
| EP | 2 314 202 A1 | 4/2011 |
| JP | 2005-501587 A | 1/2005 |
| JP | 4157839 B2 | 10/2008 |
| WO | 03/020121 A1 | 3/2003 |
| WO | WO2010100298 * | 9/2010 ............. A61B 3/028 |

OTHER PUBLICATIONS

Mar. 3, 2016 Chinese Official Action in Chinese Patent Appln. No. 201380058854.9.

* cited by examiner

FIG. 14

| Plane | Element | Radius | Glass | XSC | YSC | ZSC | ASC | BSC | CSC |
|---|---|---|---|---|---|---|---|---|---|
| 1 | STO | ∞ | Air | 0.0000 | 0.0000 | 0.0000 | 0.0000 | 0.0000 | 0.0000 |
| 3 | M1 | ∞ | REF | 0.0000 | 0.0000 | 137.308 | 45.0000 | 0.0000 | 0.0000 |
| 6 | L11 | -83.6 | NLAK22 | 0.0000 | -10.000 | 137.308 | 90.0000 | 0.0000 | 0.0000 |
| 7 | L12 | 89.3 | NSF6HT | 0.0000 | -14.000 | 137.308 | 90.0000 | 0.0000 | 0.0000 |
| 8 | L13 | 1330.5 | Air | 0.0000 | -17.500 | 137.308 | 90.0000 | 0.0000 | 0.0000 |
| 10 | L21 | -1330.5 | NSF6HT | 9.0348 | -303.94 | 128.274 | 90.0000 | 0.0000 | 0.0000 |
| 11 | L22 | -89.3 | NLAK22 | 9.0348 | -307.44 | 128.274 | 90.0000 | 0.0000 | 0.0000 |
| 12 | L23 | 83.6 | Air | 9.0348 | -311.44 | 128.273 | 90.0000 | 0.0000 | 0.0000 |
| 14 | SLM1 | ∞ | REF | 9.0348 | -458.75 | 128.274 | 88.2500 | 1.7500 | 0.0267 |
| 17 | L23 | 83.6 | NLAK22 | 9.0348 | -311.44 | 128.274 | 90.0000 | 0.0000 | 0.0000 |
| 18 | L22 | -89.3 | NSF6HT | 9.0348 | -307.44 | 128.274 | 90.0000 | 0.0000 | 0.0000 |
| 19 | L2100 | -1330.5 | Air | 9.0348 | -303.94 | 128.274 | 90.0000 | 0.0000 | 0.0000 |
| 23 | L13 | 1330.5 | NSF6HT | 0.0000 | -17.500 | 137.308 | 90.0000 | 0.0000 | 0.0000 |
| 24 | L12 | -89.3 | NLAK22 | 0.0000 | -14.000 | 137.308 | 90.0000 | 0.0000 | 0.0000 |
| 25 | L11 | -83.6 | Air | 0.0000 | -10.000 | 137.308 | 90.0000 | 0.0000 | 0.0000 |
| 28 | SLM2 | ∞ | REF | 0.0000 | 137.308 | 137.308 | 91.7500 | 1.7500 | 0.0000 |
| 30 | L11 | -83.6 | NLAK22 | 0.0000 | -10.000 | 137.308 | 90.0000 | 0.0000 | 0.0000 |
| 31 | L12 | -89.3 | NSF6HT | 0.0000 | -14.000 | 137.308 | 90.0000 | 0.0000 | 0.0000 |
| 32 | L13 | 1330.5 | Air | 0.0000 | -17.500 | 137.308 | 90.0000 | 0.0000 | 0.0000 |
| 35 | L31 | 417.8 | NSF6HT | -5.300 | -229.288 | 146.343 | 90.0000 | 0.0000 | 0.0000 |
| 36 | L32 | -42.2 | NBAF10 | -5.300 | -230.888 | 146.343 | 90.0000 | 0.0000 | 0.0000 |
| 37 | L33 | 36.9 | Air | -5.300 | -235.888 | 146.343 | 90.0000 | 0.0000 | 0.0000 |
| 38 | M2 | ∞ | REF | -5.300 | -255.888 | 146.343 | 45.0000 | 0.0000 | 0.0000 |
| 39 | SCA | ∞ | Air | -5.300 | -255.888 | 146.343 | 0.0000 | 0.0000 | 0.0000 |

FIG. 15

| Plane | Element | Radius | Material | XSC | YSC | ZSC | ASC | BSC | CSC |
|---|---|---|---|---|---|---|---|---|---|
| 1 | STO | ∞ | Air | 0.000 | 0.000 | 0.000 | 0.000 | 0.000 | 0.000 |
| 2 | M1 | ∞ | REF | 0.000 | 0.000 | 70.000 | 45.000 | 0.000 | 0.000 |
| 3 | SM1 | 300 | REF | 0.000 | -79.783 | 70.000 | 90.000 | 0.000 | 0.000 |
| 4 | SM2 | -300 | REF | 9.035 | 220.485 | 60.965 | 90.000 | 0.000 | 0.000 |
| 5 | M2 | ∞ | REF | 9.035 | 95.485 | 60.965 | 125.264 | 30.000 | 35.264 |
| 6 | SLM1 | ∞ | REF | -8.643 | 95.485 | 43.288 | 179.999 | 42.525 | -44.999 |
| 7 | M2 | ∞ | REF | 9.035 | 95.485 | 60.965 | 125.264 | 30.000 | 35.264 |
| 8 | SM2 | -300 | REF | 9.035 | 220.485 | 60.965 | 90.000 | 0.000 | 45.000 |
| 9 | SM1 | 300 | REF | 0.000 | -79.785 | 70.000 | 90.000 | 0.000 | 0.000 |
| 10 | M3 | ∞ | REF | 0.000 | 44.875 | 70.000 | 125.264 | 30.000 | 35.264 |
| 11 | SLM2 | ∞ | REF | 17.678 | 44.871 | 87.678 | 176.503 | 44.946 | -42.501 |
| 12 | M3 | ∞ | REF | 0.000 | 44.871 | 70.000 | 125.264 | 30.000 | 35.264 |
| 13 | SM1 | 300 | REF | 0.000 | -79.783 | 70.000 | 90.000 | 0.000 | 0.000 |
| 14 | SM3 | -150 | REF | -5.300 | 145.445 | 79.035 | 90.000 | 0.000 | 0.000 |
| 15 | M4 | ∞ | REF | -5.300 | 90.445 | 79.035 | 45.000 | 0.000 | 0.000 |
| 16 | SCA | ∞ | Air | -5.300 | 90.445 | 98.605 | 0.000 | 0.000 | 0.000 |

ADAPTIVE OPTICAL APPARATUS AND OPHTHALMIC APPARATUS

TECHNICAL FIELD

The present invention relates to an adaptive optical apparatus and, more particularly, to an adaptive optical apparatus which corrects wavefront aberrations, and an ophthalmic apparatus including the adaptive optical apparatus.

BACKGROUND ART

Recently, an adaptive optics (AO) technique for correcting even high-order wavefront aberrations by using an active optical element has been put into practical use and applied to various fields. In this technique, the wavefront aberration of probe light or signal light, which is generated by the characteristics of a measurement target itself or variations of the measurement environment, is sequentially measured by a wavefront sensor and corrected by a wavefront corrector such as a deformable mirror or spatial light modulator. At first, the adaptive optics (AO) was devised to improve the resolution by correcting the disturbance of the wavefront caused by fluctuations of the atmosphere at the time of astronomic observation. However, as an application field with a great effect of introduction, ophthalmic apparatuses which examine the retina of an eye are attracting attention.

As ophthalmic apparatuses, for example, there are known a fundus camera, and an SLO (Scanning Laser Ophthalmoscope) which acquires the two-dimensional image of a retina regarded as a plane. As another ophthalmic apparatus, an OCT (Optical Coherence Tomography) which noninvasively acquires the tomogram of a retina is also known and has already been in practical use. The SLO and OCT one- or two-dimensionally scan a light beam on the retina of an eye to be examined by a scanner, measure light beams reflected and backscattered by the retina in synchronism with each other, and acquire the two- or three-dimensional image of the retina.

The spatial resolution (to be referred to as a lateral resolution hereinafter) of the acquired image in the plane direction (lateral direction) of the retina is basically determined by the diameter of a beam spot scanned on the retina. To decrease the diameter of a beam spot focused on the retina, the diameter of a beam irradiating an eye to be examined is increased. However, the curved shapes and refractive indices of the cornea and crystalline lens, which is mainly in charge of refraction on the eyeball of an eye to be examined, are not uniform, and generate high-order aberrations on the wavefront of transmitted light. For this reason, even if a thick beam irradiates an eye to be examined, the spot on the retina cannot be converged to a desired diameter but spreads instead. As a result, the lateral resolution of an obtained image decreases, and the S/N ratio of an acquired image signal also decreases. Conventionally, therefore, a thin beam of about 1 mm, which is hardly influenced by the aberrations of the cornea and crystalline lens of an eye to be examined, is generally emitted to form a spot of about 20 µm on the retina.

As a means for solving this problem, the adaptive optics technique is being introduced. It has been reported so far that even if a thick beam of about 7 mm irradiates an eyeball by using this technique, the beam can be converged to about 3 µm, which is almost the diffraction limit, on the retina by wavefront correction, and a high-resolution SLO or OCT image can be acquired.

Japanese Patent No. 4157839 discloses an apparatus in which an adaptive optics system is applied to an SLO. In this adaptive optics system, a concave mirror for forming a collimated beam to irradiate a deformable mirror, and a concave mirror for receiving light reflected by the deformable mirror are adjacent to each other. This arrangement can minimize the entrance angle with respect to the concave mirror and thus can reduce the aberration of the optical system. Since ghost light reflected by the surface of an optical element forming the optical system can be suppressed, the accuracy of measurement of wavefront aberrations can be increased.

To minimize the entrance angle with respect to the concave mirror, the adaptive optical system needs to set a relatively long distance between optical elements, and the optical system becomes relatively large. The present invention provides a relatively compact adaptive optical apparatus, and an ophthalmic apparatus including the adaptive optical apparatus.

SUMMARY OF INVENTION

According to one aspect of the present invention, there is provided an adaptive optical apparatus comprising: wavefront correction means for correcting a wavefront aberration; first scanning means, arranged to be optically substantially conjugate to the wavefront correction means, for scanning light on an object in a first direction; second scanning means, arranged to be optically substantially conjugate to the wavefront correction means, for scanning light on the object in a second direction perpendicular to the first direction; and an optical element arranged in an optical path between the wavefront correction means and the first scanning means and arranged in an optical path between the first scanning means and the second scanning means.

According to another aspect of the present invention, there is provided an adaptive optical apparatus comprising: first wavefront correction means for correcting a first component of a wavefront aberration; second wavefront correction means, arranged to be optically substantially conjugate to the first wavefront correction means, for correcting a second component of the wavefront aberration that is different from the first component; first scanning means, arranged to be optically substantially conjugate to the first wavefront correction means and the second wavefront correction means, for scanning light on an object in a first direction; and an optical element arranged in an optical path between the first wavefront correction means and the second wavefront correction means and arranged in an optical path between the second wavefront correction means and the scanning means.

The present invention can provide a compact adaptive optical apparatus capable of easy adjustment, and an ophthalmic apparatus including the adaptive optical apparatus.

Further features of the present invention will become apparent from the following description of exemplary embodiments (with reference to the attached drawings).

BRIEF DESCRIPTION OF DRAWINGS

FIG. 14 is a table exemplifying optical data of the adaptive optical apparatus according to the fifth embodiment; and FIG. 15 is a table exemplifying optical data of the adaptive optical apparatus according to the sixth embodiment.

DESCRIPTION OF EMBODIMENTS

Preferred embodiments of the present invention will now be exemplarily described in detail with reference to the accompanying drawings. It should be noted that the building components set forth in these embodiments are merely examples, and the technical scope of the present invention is defined by claims and is not limited by each embodiment described below.

First Embodiment: Arrangement in which Optical Elements (Lenses 61 and 62) are Arranged in Optical Path Between Wavefront Corrector 1 and First Reflection Scanner 32 and Optical Path Between First Reflection Scanner 32 and Second Reflection Scanner 31

Figure 1:
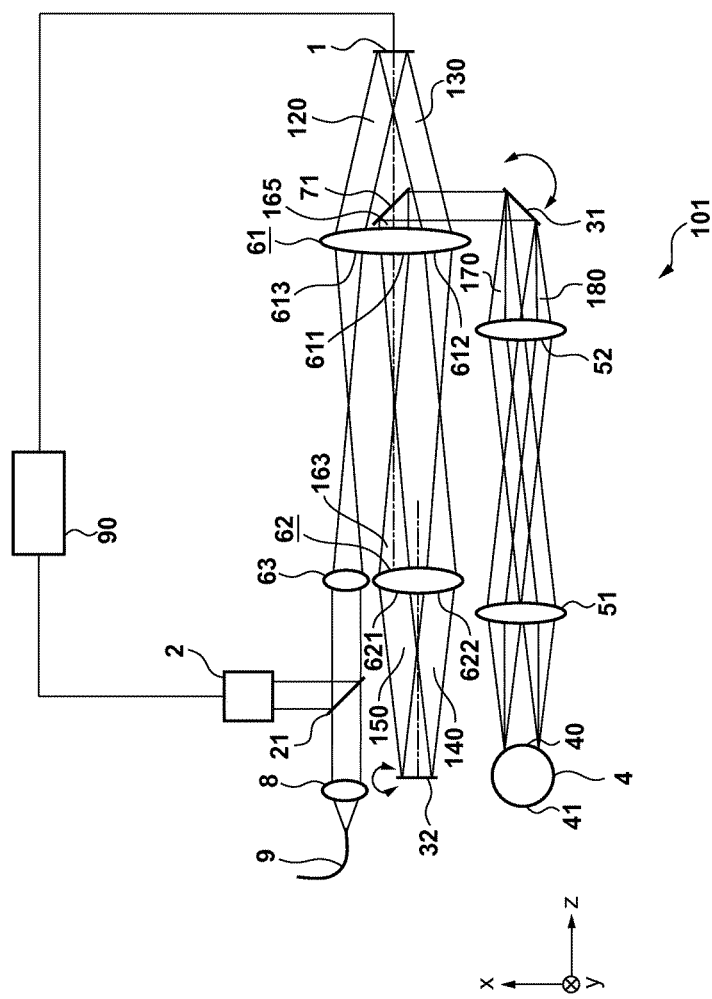
FIG. 1 is a view showing the arrangement of an adaptive optical apparatus according to the first embodiment of the present invention.

FIG. 1 exemplifies the arrangement of an adaptive optics SLO 101 (adaptive optical apparatus) according to the first embodiment of the present invention. Illumination light (measurement light) propagating through an optical fiber 9 from a light source (not shown) emerges from the end face of the optical fiber 9. The light (measurement light) emerging from the end face of the optical fiber 9 is collimated by a collimator lens 8, passes through a half mirror 21, and is collimated again via lenses 63 and 61. A collimated light flux 120 irradiates a reflection wavefront corrector 1. The wavefront corrector 1 can be, for example, a deformable mirror, a liquid crystal spatial light modulator using a liquid crystal, or LCOS (Liquid Crystal On Silicon).

A light flux 130 reflected by the wavefront corrector 1 is converged again by the lens 61 and collimated again by a lens 62. A collimated light flux 140 irradiates a first reflection scanner 32 (first scanner). A first pupil conjugate optical system formed from the lenses 61 and 62 gives a pupil conjugate relationship to the wavefront corrector 1 and first reflection scanner 32. The first reflection scanner 32 scans an irradiation light flux in the y direction (direction perpendicular to the paper surface). The y direction is a direction perpendicular to an irradiation direction in which light (measurement light) irradiates an object (for example, the fundus or anterior ocular segment of a human or the interior of the body of a human; an eye 4 to be examined will be explained). The y direction is defined as the first direction. In the arrangement of the adaptive optical apparatus shown in FIG. 1, the first reflection scanner 32 is arranged to be optically almost conjugate to the wavefront corrector 1, and scans light on an object in the first direction (y direction in FIG. 1).

Note that a light flux 150 scanned by the first reflection scanner 32 is converged again by the lens 62, irradiates the lens 61 for the third time, and is collimated again (a light flux 160). At this time, the light flux 160 passes through a region of the lens 61 that is different from regions irradiated for the first and second times, and then is reflected by a mirror 71. In the optical path of the light reflected by the mirror 71, a second reflection scanner 31 (second scanner) is arranged at a position (position equivalent to the wavefront corrector 1) corresponding to the pupil of the lens 61. The first reflection scanner 32 and second reflection scanner 31 have an optically conjugate relationship. Hence, the light flux 150 scanned by the first reflection scanner 32 is converged on the second reflection scanner 31. The second reflection scanner 31 scans an irradiation light flux in the x direction. The x direction is a direction perpendicular to the irradiation direction in which measurement light irradiates the eye 4 to be examined, and the first direction (direction perpendicular to the paper surface). The x direction is defined as the second direction. In the arrangement of the adaptive optical apparatus shown in FIG. 1, the second reflection scanner 31 is arranged to be optically almost conjugate to the wavefront corrector 1, and scans light on an object in the second direction (x direction in FIG. 1) perpendicular to the first direction (y direction in FIG. 1).

Common optical elements (lenses 51 and 52: second optical elements) for transmitting light scanning an eye to be examined and transmitting light traveling from it are arranged in the optical path between the second reflection scanner 31 (second scanner) and the eye 4 to be examined. Light fluxes 170 and 180 scanned by the second reflection scanner 31 irradiate a pupil 40 of the eye 4 to be examined via a second pupil conjugate optical system (second optical system) formed from the lenses 51 and 52 (second optical elements). A retina 41 can be two-dimensionally scanned in the x and y directions by performing scanning of the second reflection scanner 31 in synchronism with scanning of the first reflection scanner 32. The light reflected by the eye to be examined irradiates the second reflection scanner 31 via regions of the lenses 51 and 52 that are different from those in irradiation.

Figure 5:
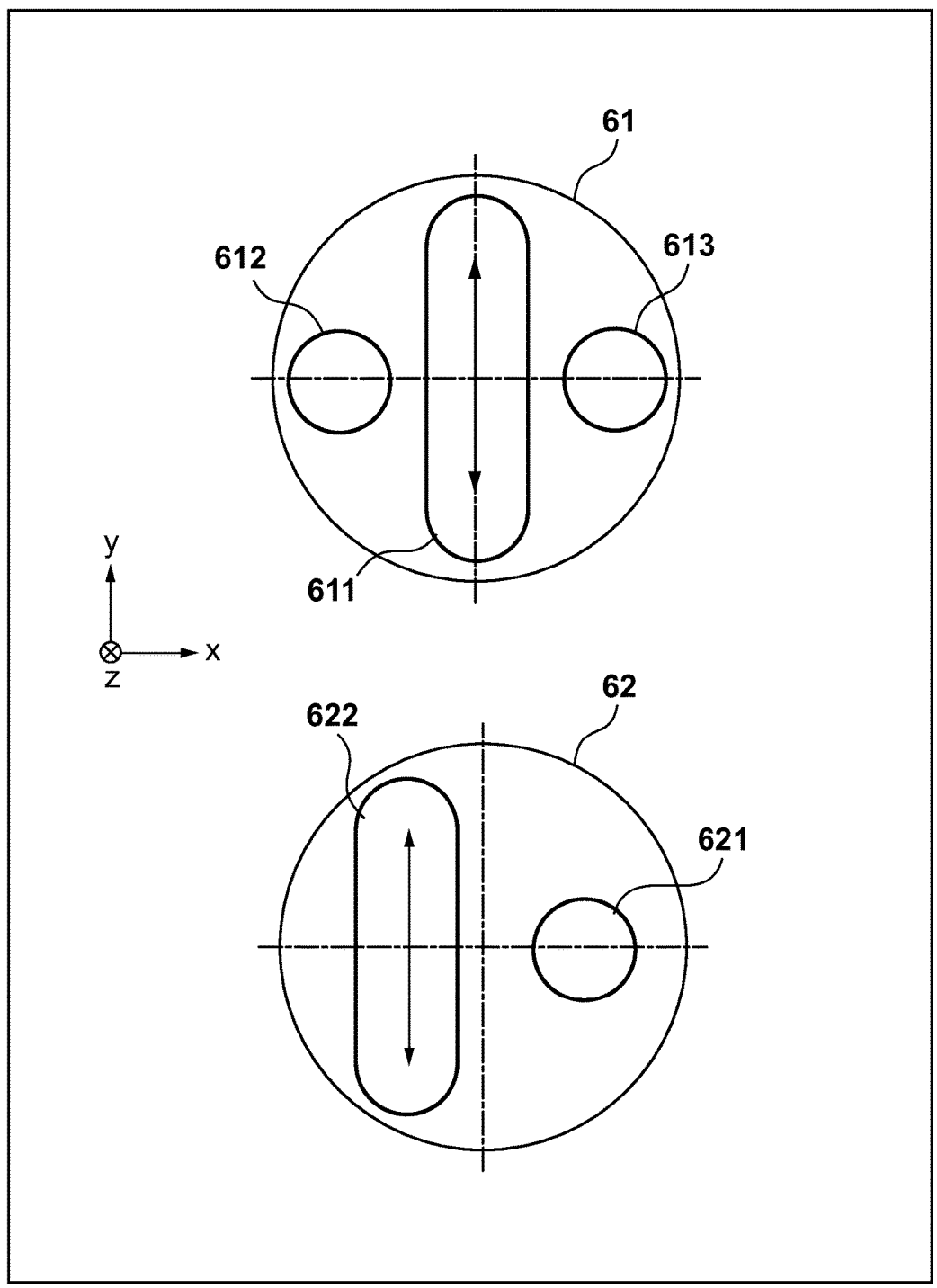
FIG. 5 is a view showing a region in a lens through which a light flux passes in the adaptive optical apparatus according to the first embodiment.

FIG. 5 shows allocation of passage regions through which light fluxes pass in the lenses 61 and 62 of the first pupil conjugate optical system. As for the lenses 51 and 52, for example, passage regions can be allocated similarly to the lens 62.

A light flux propagating from the end face of the optical fiber 9 toward the eye to be examined will be exemplified. A light flux traveling from the lens 63 passes through a region 613 of the lens 61 when viewed from the wavefront corrector 1, and emerges as the light flux 120 from the region 613 of the lens 61. The light flux from the light source irradiates the wavefront corrector 1 via the region 613.

The light flux 120 is reflected by the wavefront corrector 1, and the reflected light flux 130 irradiates the lens 61 again. The light flux 130 passes through a region 612 (first region) of the lens 61. The light flux reflected by the wavefront corrector 1 via the region 612 (first region) irradiates the first reflection scanner 32 (first scanner). The light flux having passed through the region 612 of the lens 61 irradiates the lens 62, and emerges as the light flux 140 from a region 622 of the lens 62. The light flux 140 is scanned in the y direction by the first reflection scanner 32. The scanned light flux 150 irradiates the lens 62 again, and passes through a region 621 of the lens 62. A light flux 163 emerging from the region 621 of the lens 62 irradiates the lens 61 for the third time, and passes through a region 611 of the lens 61. A light flux 165 emerging from the region 611 (second region) of the lens 61 is reflected by the mirror 71. The light flux reflected by the first reflection scanner 32 (first scanner) via the region 611 (second region) irradiates the second reflection scanner 31 (second scanner).

The anterior ocular segment of the eye 4 to be examined gives aberration to return light which has irradiated the retina 41 and has been reflected and backscattered. Then, the return light propagates through an optical path reverse to the above-described optical path. The wavefront corrector 1 reflects the light reflected by the eye 4 to be examined. The light reflected by the wavefront corrector 1 irradiates a wavefront detector 2 via the region 613 (third region) different from the region 612 (first region) and region 611 (second region) in the lens 61.

The region 611 (second region) is a region at the center on the surface of the optical element (on the surface of the lens 61). The region 612 (first region) and region 613 (third region) are different end regions on the surface of the optical element (on the surface of the lens 61). The region 611 (second region) is positioned between the different end regions (between the regions 612 and 613). By allocating the passage regions in this fashion, maximum regions can be ensured on the surface of the optical element (lens 61) for transmitting light fluxes respectively scanned by the first reflection scanner 32 and second reflection scanner 31. Since maximum regions can be ensured on the surface of the optical element for transmitting scanned light fluxes without upsizing the optical element (lens 61), the adaptive optical apparatus can be downsized.

Return light having passed through the region 613 is branched by the half mirror 21. Part of the return light enters the wavefront detector 2, and its wavefront is detected. Information about the detected wavefront is sent to an information processing unit 90. The information processing unit 90 calculates a wavefront aberration based on the wavefront information acquired from the wavefront detector 2, obtaining the wavefront shape (correction instruction value) of the wavefront corrector 1 to cancel the wavefront aberration. Then, the information processing unit 90 instructs the wavefront corrector 1 to deform the shape of the reflection surface. In accordance with this correction instruction value, the wavefront corrector 1 is driven to change the shape of the reflection surface.

The wavefront corrector 1 driven for correction gives a counter aberration to light (measurement light) emerging from the end face of the optical fiber 9 in order to cancel the wavefront aberration. The counter aberration-applied measurement light propagates through the optical path of the adaptive optics SLO 101, and irradiates the pupil 40 of the eye 4 to be examined. The counter aberration is canceled by the aberration of the anterior ocular segment of the eye 4 to be examined, and the measurement light is focused on the retina 41 with less aberration. Aberration is generated in return light from the retina 41 when the light emerges from the anterior ocular segment. However, the wavefront corrector 1 cancels the aberration of the anterior ocular segment, and the return light satisfactorily forms an image on the end face of the optical fiber 9 via the collimator lens 8 with less aberration. The return light propagating through the optical fiber 9 is branched by a fiber coupler (not shown), and detected as an image signal by a photodetector such as a photodiode or photomultiplier. A two-dimensional image is generated in synchronism with the light flux scanning timing.

In the first embodiment, the wavefront corrector 1, first reflection scanner 32, second reflection scanner 31, and eye 4 to be examined are arranged at pupil conjugate positions in the pupil conjugate optical system formed from the lenses 61 and 62 and the pupil conjugate optical system formed from the lenses 51 and 52. When lens pairs are used between the four respective pupil conjugate positions, like a conventional arrangement, eight lenses are required.

An optical system (pupil conjugate optical system) including common optical elements is arranged in the optical path (conjugate optical path) between the wavefront corrector 1 and the first reflection scanner 32 and the optical path (conjugate optical path) between the first reflection scanner 32 and the second reflection scanner 31. That is, the two conjugate optical paths share one pupil conjugate optical system formed from the lenses 61 and 62.

An optical system (pupil conjugate optical system) including common optical elements for transmitting light is arranged in the optical path between the second reflection scanner 31 and the eye 4 to be examined.

With this arrangement, the pupil conjugate optical system formed from the lenses 61 and 62 and the pupil conjugate optical system formed from the lenses 51 and 52 can be configured by four optical elements (lenses). The overall adaptive optics SLO 101 can be configured by five optical elements (lenses), including the lens 63 between the wavefront detector 2 and the wavefront corrector 1.

By commonly using the optical elements (lenses), a compact adaptive optical apparatus capable of easy adjustment can be provided regardless of a large number of pupil conjugate positions in the adaptive optical apparatus.

The common use of the lenses can reduce the area of the overall adaptive optical apparatus which tends to become large in the conventional arrangement. Also, the cost can be reduced thanks to reduction of the number of components and reduction of the number of adjustment points. Although the first embodiment has exemplified the SLO, the adaptive optical apparatus is applicable to even an ophthalmic apparatus such as an OCT or fundus camera.

In a reflection optical system having a long optical path, the sensitivity to the tolerance of adjustment of a mirror is high. Thus, adjustment of each mirror is indispensable, and the number of steps for adjustment may impose a heavy burden. However, according to the arrangement of the first embodiment, even when the adaptive optical system is employed, adjustment is easy with a compact size. An adaptive optical apparatus which implements a size and cost appropriate as a commercial apparatus can be provided.

Figure 2:
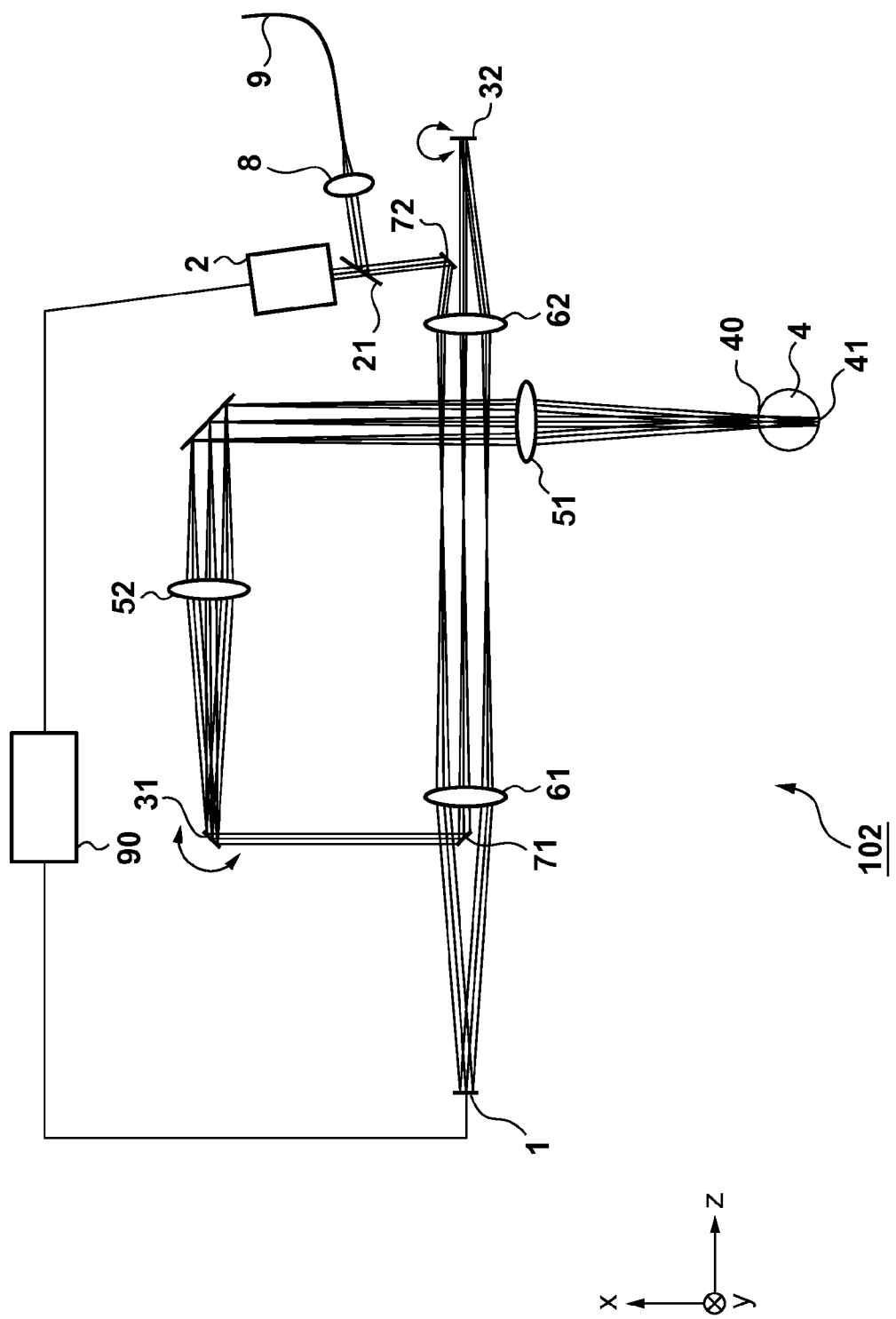
FIG. 2 is a view showing the arrangement of an adaptive optical apparatus according to the second embodiment of the present invention.

Second Embodiment: Arrangement in which
Optical Path Between Wavefront Detector 2 and
Wavefront Corrector 1 is Added to Arrangement of
First Embodiment FIG. 2 exemplifies the arrangement of an adaptive optics SLO 102 (adaptive optical apparatus) according to the second embodiment of the present invention. The first and second pupil conjugate optical systems are the same as those in the first embodiment. In the second embodiment, the first pupil conjugate optical system formed from lenses 61 and 62 is commonly used additionally for the conjugate optical path between a wavefront detector 2 and a wavefront corrector 1.

Illumination light emerging from the end face of an optical fiber 9 is deflected by a mirror 72 via a collimator lens 8 and half mirror 21, and irradiates the lens 62. After that, the light enters an eye 4 to be examined through the same path as that in the first embodiment. Return light from a retina 41 propagates through a reverse optical path, and is reflected by the mirror 72 via the lens 62. Part of the light passes through the half mirror 21 and enters the wavefront detector 2, while the remaining light is reflected and returns to the end face of the optical fiber 9.

The detection surface of the wavefront detector 2 is set at a position equivalent to a first reflection scanner 32, that is, at the pupil conjugate position of the first pupil conjugate optical system. Therefore, one pupil conjugate optical system formed from the lenses 61 and 62 is shared between three conjugate optical paths between the wavefront corrector 1 and the first reflection scanner 32, between the first reflection scanner 32 and a second reflection scanner 31, and between the wavefront detector 2 and the wavefront corrector 1.

The diameter of a collimated light flux emerging from the collimator lens 8 is 3 mm, and the detection range of a light flux of return light to be detected by the wavefront detector 2 is also set to 3 mm. The focal distance of the lens 61 is set to be double the focal distance of the lens 62 so that the diameter of an irradiation light flux to the wavefront corrector 1 becomes 6 mm.

A light flux of a 3-mm diameter irradiates a resonance scanner mirror serving as the first reflection scanner 32, and a light flux of a 6-mm diameter irradiates a galvano-scanner mirror serving as the second reflection scanner 31. In addition, the focal distance of a lens 51 is set to be 2.2 times larger than the focal distance of a lens 52 so that a light flux of a 6.6-mm diameter irradiates the pupil. If wavefront aberration correction is performed ideally, a spot about 3 μm in diameter irradiates the retina.

Figure 6:
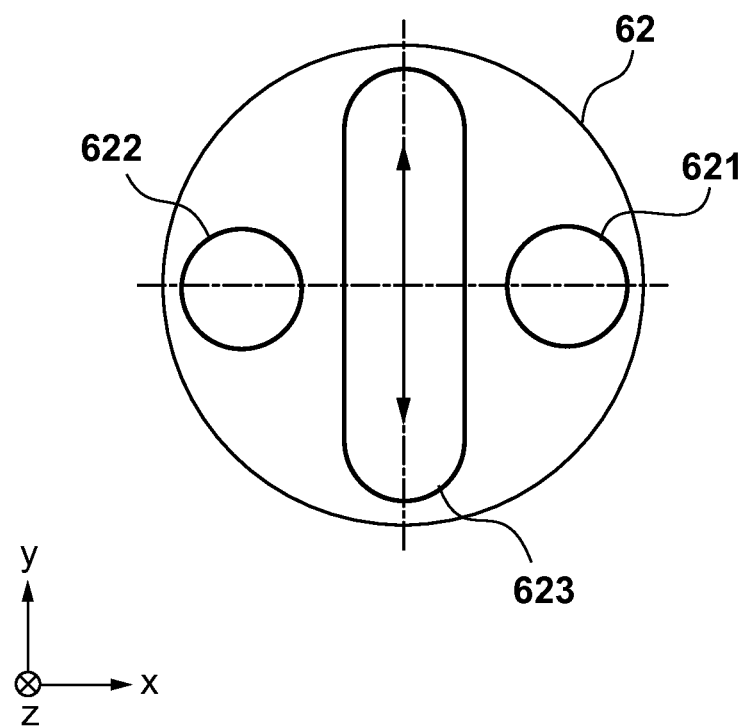
FIG. 6 is a view showing a region in a lens through which a light flux passes in the adaptive optical apparatus according to the second and third embodiments.

FIG. 6 shows allocation of three passage regions through which light fluxes pass in the lens 62 of the first pupil conjugate optical system. This also applies to the lens 61. A light flux irradiates a region 621 of the lens 62, and emerges from the region 621 of the lens 62. The return light flux reflected by the wavefront corrector 1 passes through a region 622 of the lens 62. The light flux emerging from the region 622 of the lens 62 irradiates the first reflection scanner 32. The light flux scanned by the first reflection scanner 32 passes through a region 623 of the lens 62. Allocation of regions through which light fluxes pass in the lens 61 is the same as that for the lens 62.

The region 623 is a region at the center on the surface of the optical element (on the surface of the lens 62). The regions 621 and 622 are different end regions on the surface of the optical element (on the surface of the lens 62). The region 623 is positioned between the different end regions (between the regions 621 and 622). By allocating the passage regions in this manner, maximum regions can be ensured on the surface of the optical element (lens 62) for transmitting light fluxes respectively scanned by the first reflection scanner 32 and second reflection scanner 31. Since maximum regions can be ensured on the surface of the optical element for transmitting scanned light fluxes without upsizing the optical element (lens 62), the adaptive optical apparatus can be downsized.

The wavefront detector 2, wavefront corrector 1, first reflection scanner 32, second reflection scanner 31, and eye 4 to be examined are arranged at pupil conjugate positions in the pupil conjugate optical system formed from the lenses 61 and 62 and the pupil conjugate optical system formed from the lenses 51 and 52. Five pupil conjugate positions are set. When optical element pairs are used between the respective pupil conjugate positions, like a conventional arrangement, a total of 10 optical elements are required.

In the second embodiment, an optical system including common optical elements for transmitting light is arranged in the optical path between the wavefront detector 2 and the wavefront corrector 1, the optical path between the wavefront corrector 1 and the first reflection scanner 32, and the optical path between the first reflection scanner 32 and the second reflection scanner 31. Further, an optical system including common optical elements for transmitting light is arranged in the optical path between the second reflection scanner 31 and the eye 4 to be examined.

With this arrangement, the overall adaptive optics SLO 102 can be configured by four optical elements (lenses). The number of necessary optical elements can be decreased to be half or less than that in the conventional arrangement.

By commonly using the optical elements, a compact adaptive optical apparatus capable of easy adjustment can be provided regardless of a large number of pupil conjugate positions in the adaptive optical apparatus. In addition, the common use of the lenses can reduce the area of the overall AO optical system which tends to become large in the conventional arrangement. Also, the cost can be reduced thanks to reduction of the number of components and reduction of the number of adjustment points. Although the second embodiment has exemplified the SLO, the adaptive optical apparatus is applicable to even an ophthalmic apparatus such as an OCT or fundus camera.

Third Embodiment: Arrangement Using Mirror as Optical Element

The first and second embodiments use lenses as optical elements. However, especially when an ophthalmic apparatus adopts an adaptive optical apparatus, return light from a retina is very weak. Thus, when the lenses are used, light reflected by the lens surface may irradiate the wavefront corrector. In a state in which light reflected by the lens surface irradiates the wavefront detector, no wavefront aberration can be measured accurately. To prevent this, the adaptive optical apparatus often uses an eccentric reflection optical system in which return of light reflected by the lens surface hardly occurs. In the third embodiment, the arrangement of an adaptive optics SLO 103 (adaptive optical apparatus) using a mirror as an optical element will be exemplified with reference to FIG. 3.

Figure 3:
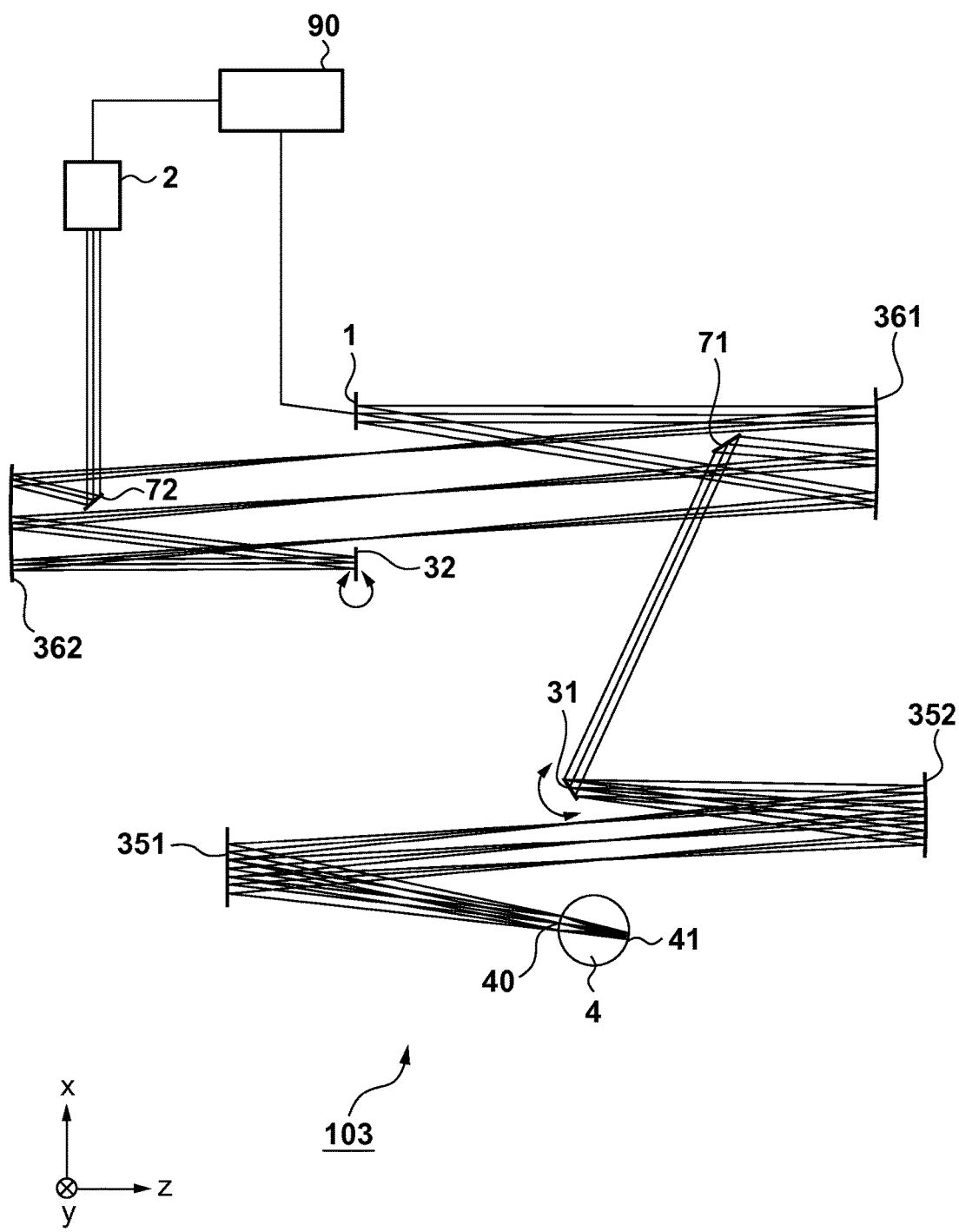
FIG. 3 is a view showing the arrangement of an adaptive optical apparatus according to the third embodiment of the present invention.

In FIG. 3, the basic arrangement of the adaptive optical apparatus, an optical device used, and the like comply with the second embodiment. However, reference numerals 351, 352, 361, and 362 denote not lenses but concave mirrors. Since the concave mirrors are used, the respective concave mirrors are arranged to be eccentric in order to separate irradiation light toward the mirror and light reflected by the mirror. Deflection mirrors 71 and 72 are installed in the regions of light fluxes traveling between the concave mirrors 361 and 362. The concave mirrors 361 and 362 form a common pupil conjugate optical system. An optical system (pupil conjugate optical system) including common optical elements for transmitting light is arranged in three conjugate optical paths between a wavefront corrector 1 and a first reflection scanner 32, between the first reflection scanner 32 and a second reflection scanner 31, and between a wavefront detector 2 and the wavefront corrector 1. Also, an optical system (pupil conjugate optical system) including common optical elements for transmitting light is arranged in the optical path between the second reflection scanner 31 and an eye 4 to be examined.

Allocation of reflection regions on the concave mirror 362 for reflecting a light flux when viewed from the first reflection scanner 32 is the same as that in FIG. 6.

According to the third embodiment, unwanted light to the surface of the wavefront detector can be prevented. By commonly using the optical elements, a compact adaptive optical apparatus capable of easy adjustment can be provided regardless of a large number of pupil conjugate positions in the adaptive optical apparatus.

Fourth Embodiment: Arrangement in which Optical Elements (Lenses 61 and 62) are Arranged in Optical Path Between First Wavefront Corrector 11 and Second Wavefront Corrector 12 and Optical Path Between Second Wavefront Corrector 12 and First Reflection Scanner 32

Figure 4:
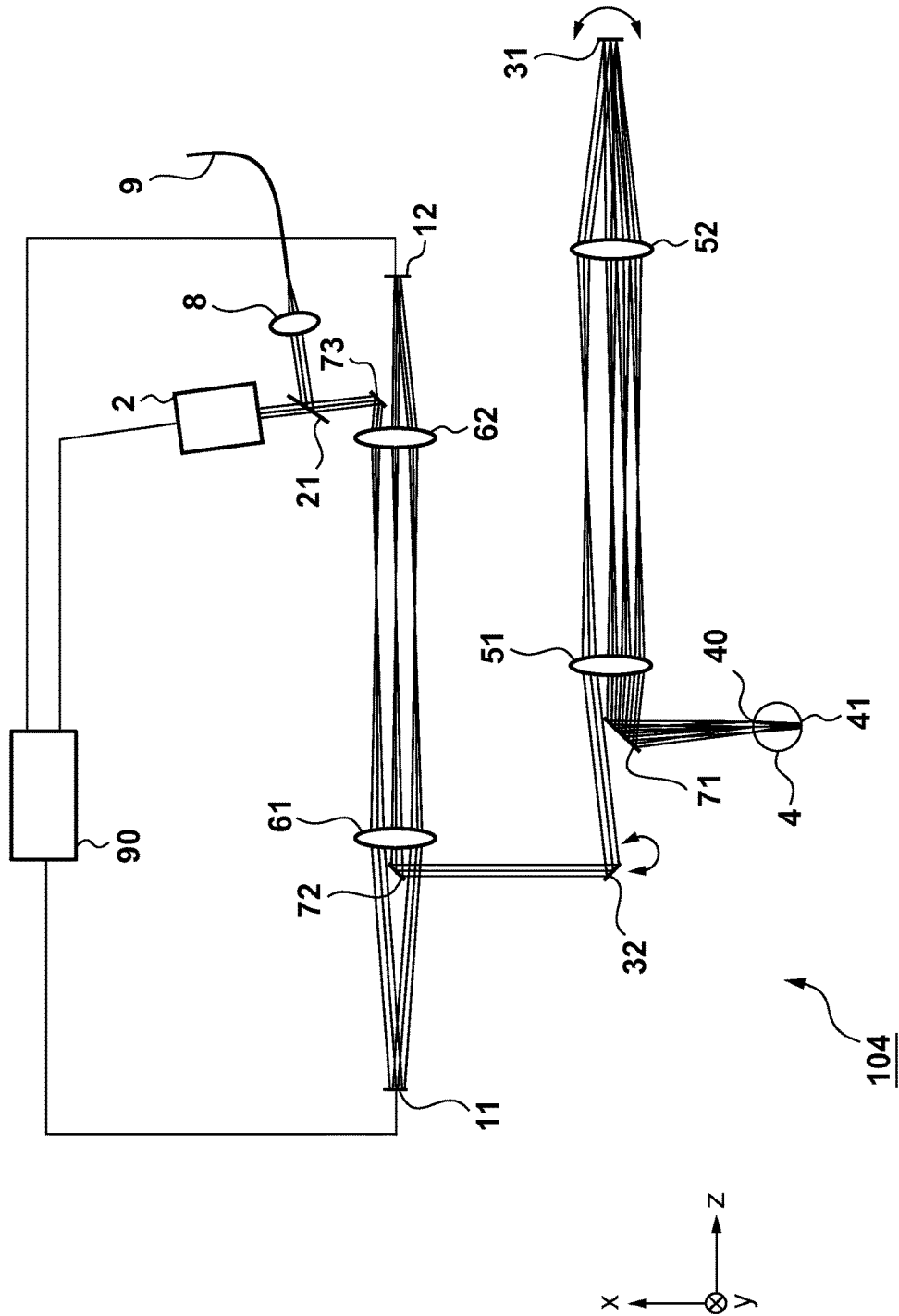
FIG. 4 is a view showing the arrangement of an adaptive optical apparatus according to the fourth embodiment of the present invention.

FIG. 4 shows an adaptive optics SLO 104 (adaptive optical apparatus) according to the fourth embodiment of the present invention. The adaptive optics SLO 104 according to the fourth embodiment uses two wavefront correctors, that is, a first wavefront corrector 11 and second wavefront corrector 12. Aberrations to be corrected can be distributed to the respective wavefront correctors in accordance with the characteristics of the wavefront correctors. The fourth embodiment exemplifies two wavefront correctors. However, the gist of the present invention is not limited to this example, and the wavefront aberration of light reflected by an eye to be examined can be corrected by using three or more wavefront correctors.

For example, a deformable mirror for correcting a second-order aberration (first component of the wavefront aberration) such as defocus or astigmatism aberration is used as the first wavefront corrector 11. A deformable mirror for correcting a third- or higher-order aberration (second component of the wavefront aberration) is used as the second wavefront corrector 12. Aberrations to be corrected can be distributed to the respective wavefront correctors. Alternatively, a liquid crystal phase modulator for correcting a vertically polarized component (first component of the wavefront aberration) may be used as the first wavefront corrector 11, and a liquid crystal phase modulator for correcting a horizontally polarized component (second component of the wavefront aberration) may be used as the second wavefront corrector 12.

One pupil conjugate optical system formed from lenses 61 and 62 is shared between three conjugate optical paths between a wavefront detector 2 and the first wavefront corrector 11, between the first wavefront corrector 11 and the second wavefront corrector 12, and between the second wavefront corrector 12 and a first reflection scanner 32.

The wavefront detector 2, first wavefront corrector 11, second wavefront corrector 12, and first reflection scanner 32 are arranged at pupil conjugate positions in one pupil conjugate optical system (first pupil conjugate optical system) formed from the lenses 61 and 62. In the arrangement of the adaptive optical apparatus shown in FIG. 4, the second wavefront corrector 12 is arranged to be optically almost conjugate to the first wavefront corrector 11, and corrects the second component of the wavefront aberration different from the first component of the wavefront aberration. When deformable mirrors are used as the first wavefront corrector 11 and second wavefront corrector 12, the first component of the wavefront aberration contains a second-order aberration such as defocus or astigmatism aberration, and the second component of wavefront aberration contains a third- or higher-order aberration.

When liquid crystal phase modulators are used as the first wavefront corrector 11 and second wavefront corrector 12, the first component of the wavefront aberration contains, for example, a vertically polarized component, and the second component of the wavefront aberration contains a horizontally polarized component.

The first reflection scanner 32 is arranged to be optically almost conjugate to the first wavefront corrector 11 and second wavefront corrector 12. The first reflection scanner 32 scans light on an object in the first direction (y direction perpendicular to the paper surface of FIG. 4).

One pupil conjugate optical system formed from lenses 51 and 52 is shared between two conjugate optical paths between the first reflection scanner 32 and a second reflection scanner 31 and between the second reflection scanner 31 and an eye 4 to be examined.

The first reflection scanner 32, second reflection scanner 31, and eye 4 to be examined are arranged at pupil conjugate positions in one pupil conjugate optical system (second pupil conjugate optical system) formed from the lenses 51 and 52.

Illumination light emerging from a collimator lens 8 is guided to the first wavefront corrector 11 via a half mirror 21, a mirror 73, and the lenses 62 and 61, similar to the second embodiment. A light flux reflected by the first wavefront corrector 11 is guided again to the second wavefront corrector 12 via the lenses 61 and 62. The light flux reflected by the second wavefront corrector 12 is deflected for the third time by a mirror 72 via the lenses 62 and 61, and irradiates the first reflection scanner 32.

After that, the first reflection scanner 32 scans the irradiation light flux in the y direction (direction perpendicular to the paper surface). The light flux scanned by the first reflection scanner 32 irradiates the second reflection scanner 31 via the lenses 51 and 52. The second reflection scanner 31 scans the irradiation light flux in the x direction. The light flux scanned by the second reflection scanner 31 is deflected again by a mirror 71 via the lenses 51 and 52, and irradiates a pupil 40 of the eye 4 to be examined.

The retina 41 can be two-dimensionally scanned in the x and y directions by performing scanning of the second reflection scanner 31 in synchronism with scanning of the first reflection scanner 32. Return light which has irradiated the retina 41 and has been reflected and backscattered propagates through an optical path reverse to the above-described optical path. The half mirror 21 branches the return light. Part of the return light enters the wavefront detector 2, and the wavefront detector 2 detects the wavefront. The remaining return light is reflected by the half mirror 21, and forms an image on the end face of an optical fiber 9 via the collimator lens 8. The return light propagating through the optical fiber 9 is branched by a fiber coupler (not shown), and detected as an image signal by a photodetector such as a photodiode or photomultiplier. A two-dimensional image is formed in synchronism with the light flux scanning timing.

Information about the wavefront detected by the wavefront detector 2 is sent to an information processing unit 90. The information processing unit 90 calculates a wavefront aberration based on the wavefront information acquired from the wavefront detector 2, obtaining the wavefront shapes (correction instruction values) of the first wavefront corrector 11 and second wavefront corrector 12 to cancel the wavefront aberration. Then, the information processing unit 90 instructs the first wavefront corrector 11 and second wavefront corrector 12 to deform the shapes of the reflection surfaces. In accordance with the respective correction instruction values, the first wavefront corrector 11 and second wavefront corrector 12 are driven to change the shapes of the reflection surfaces, and perform wavefront correction.

Figure 7:
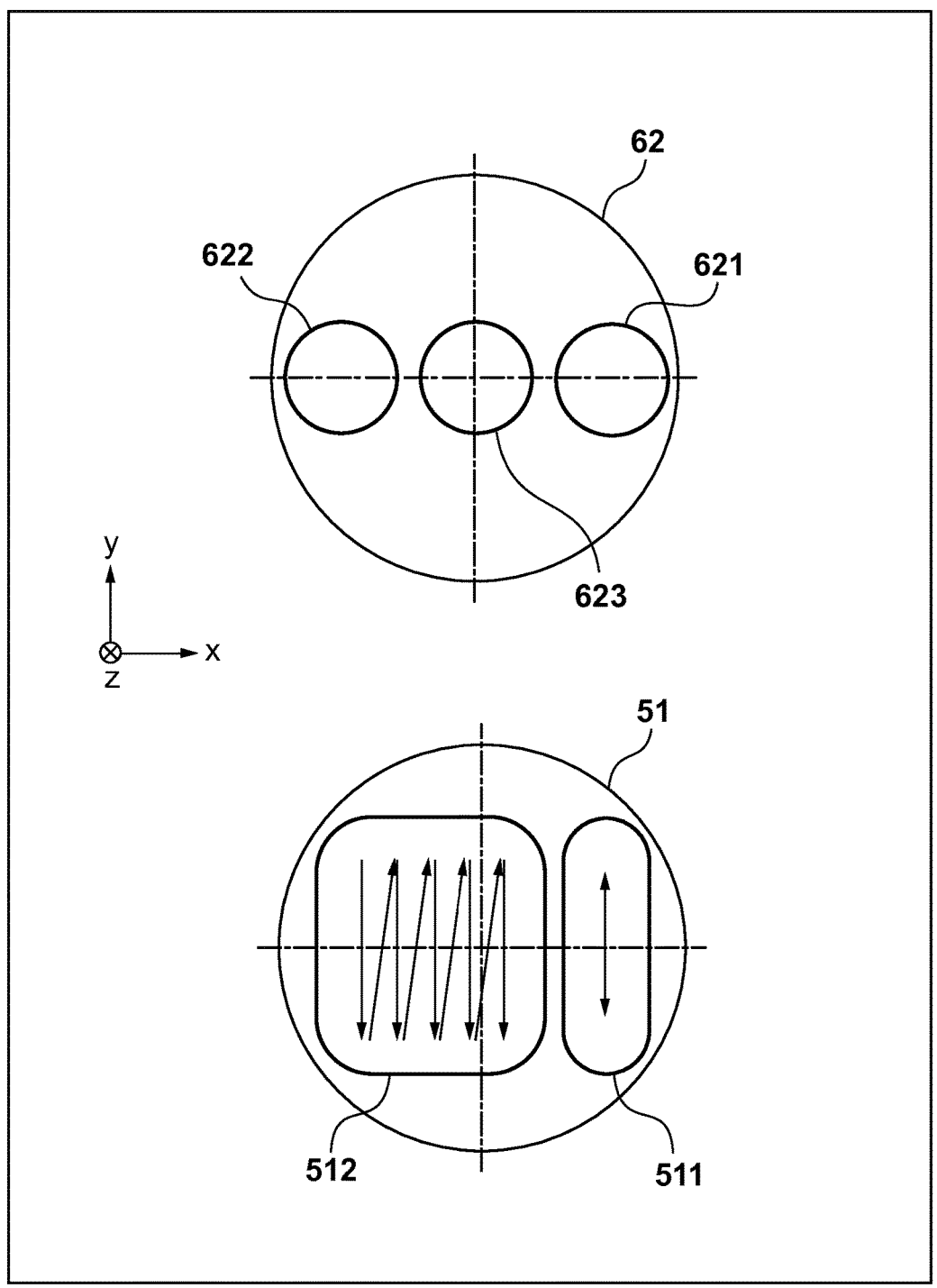
FIG. 7 is a view showing a region in a lens through which a light flux passes in the adaptive optical apparatus according to the fourth embodiment.

FIG. 7 shows allocation of passage regions through which light fluxes pass in the lenses 61, 62, and 51. As for the lens 62 of the first pupil conjugate optical system, an illumination beam reflected by the mirror 73 when viewed from the second wavefront corrector 12 passes through a region 621 of the lens 62. The light flux emerging from the region 621 is reflected by the first wavefront corrector 11 and passes through a region 622 of the lens 62. The light flux emerging from the region 622 is reflected by the second wavefront corrector 12 and passes through a region 623 of the lens 62. The light flux also passes through similar regions of the lens 61.

As for the lens 51 (second optical element) of the second pupil conjugate optical system, a light flux scanned in the y direction by the first reflection scanner 32 when viewed from the first reflection scanner 32 passes through a region 511 of the lens 51 when viewed from the first reflection scanner 32. The light flux emerging from the region 511 (first region) of the lens 51 is further scanned in the x direction by the second reflection scanner 31, passes through a region 512 (second region) of the lens 51, and irradiates the eye 4 to be examined via the mirror 71. In accordance with the allocation, the light flux passes through regions of the lens 52 similar to those of the lens 51. In the lens 51, to transmit a light flux scanned in the two-dimensional directions (x and y directions), the area of the region 512 (second region) is larger than that of the region 511 (first region) for transmitting a light flux in the one-dimensional direction (y direction).

The above-described arrangement has six pupil conjugate positions (wavefront detector 2, first wavefront corrector 11, second wavefront corrector 12, first reflection scanner 32, second reflection scanner 31, and eye 4 to be examined). When optical element pairs (lens pairs) are used between the respective pupil conjugate positions, like a conventional arrangement, 12 optical elements (lenses) are required.

According to the arrangement of the fourth embodiment, the overall adaptive optics SLO 104 can be configured by four optical elements (lenses). The number of necessary optical elements can be decreased to be half or less than that in the conventional arrangement. By commonly using the optical elements, a compact adaptive optical apparatus can be provided regardless of a large number of pupil conjugate positions in the adaptive optical apparatus.

The common use of the lenses can reduce the area of the overall AO optical system which tends to become large in the conventional arrangement. Also, the cost can be reduced thanks to reduction of the number of components and reduction of the number of adjustment points. Although the fourth embodiment has exemplified the SLO, the adaptive optical apparatus is applicable to even an ophthalmic apparatus such as an OCT or fundus camera.

Fifth Embodiment: Arrangement Using Liquid Crystal SLM as Wavefront Corrector

Figure 8:
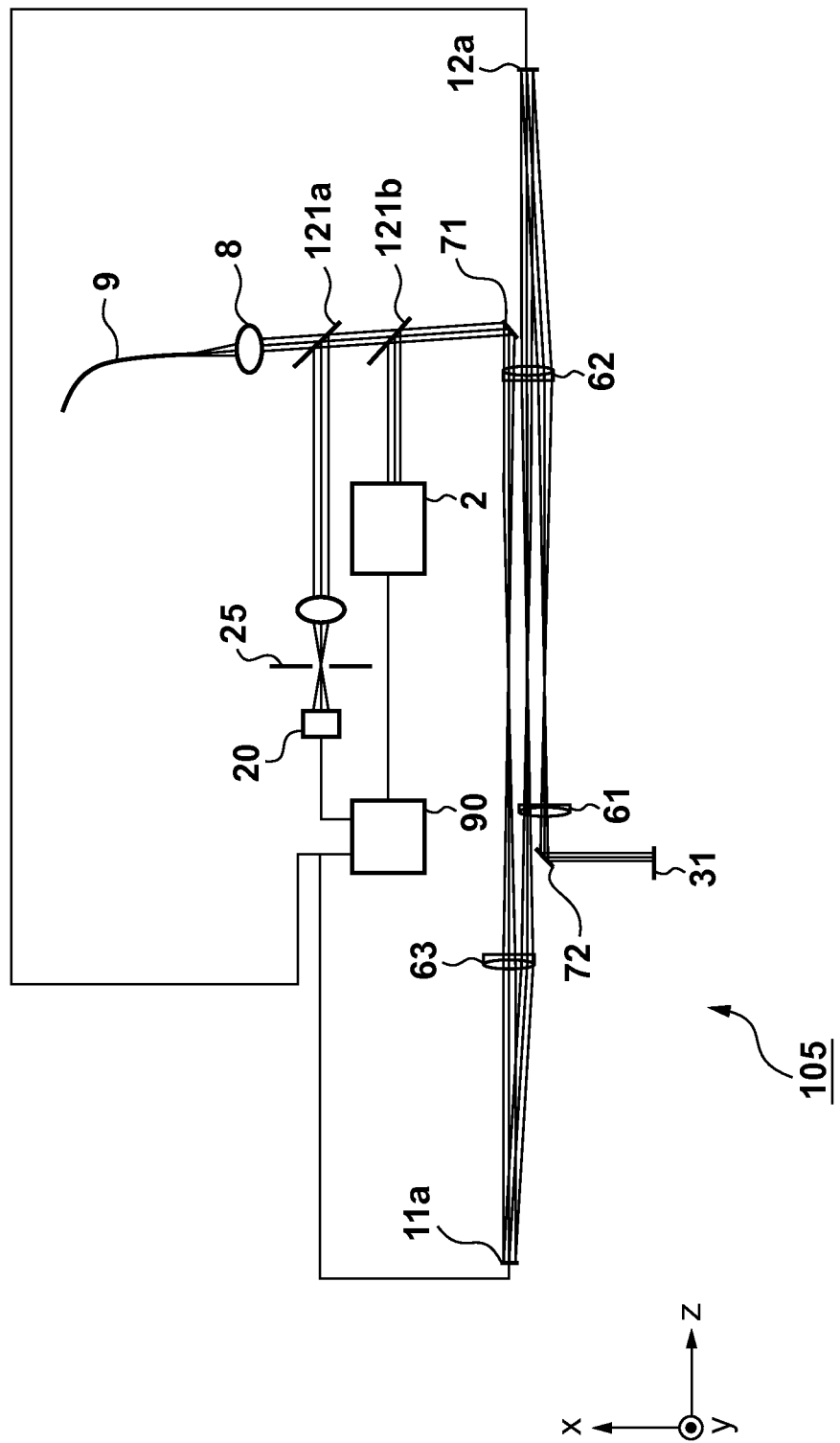
FIG. 8 is a view showing the x-z section of an adaptive optical apparatus according to the fifth embodiment.
Figure 9:
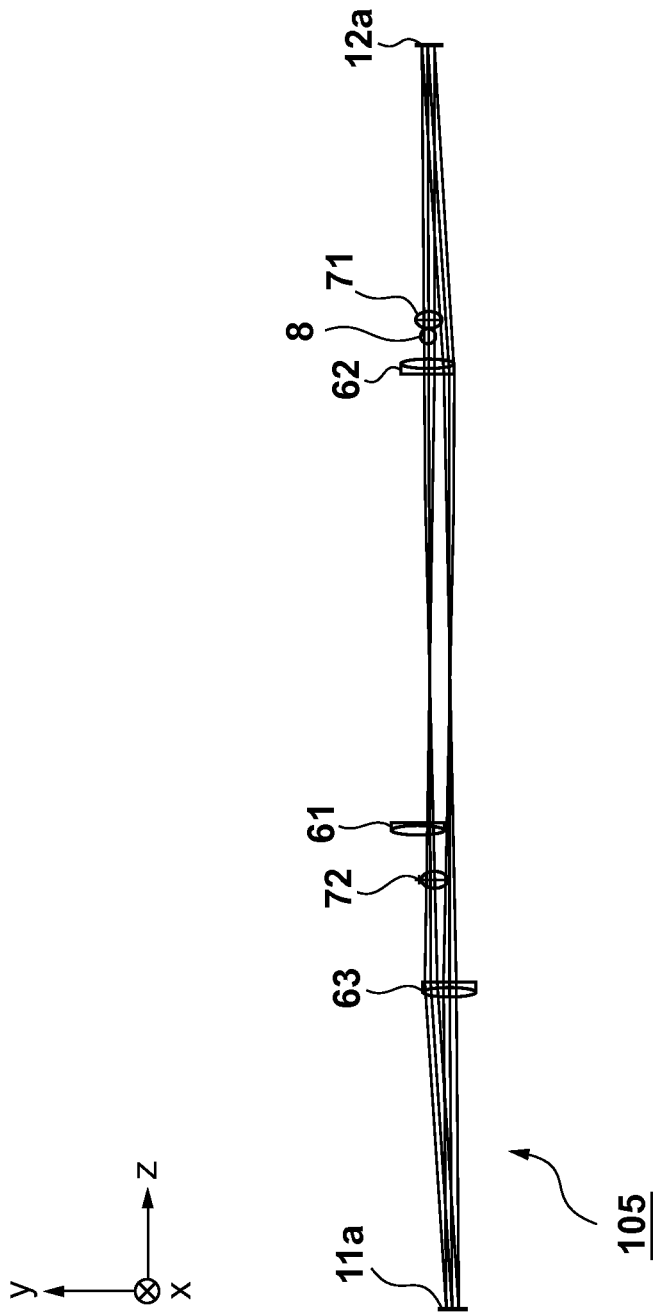
FIG. 9 is a view showing the y-z section of the adaptive optical apparatus according to the fifth embodiment.
Figure 10A:
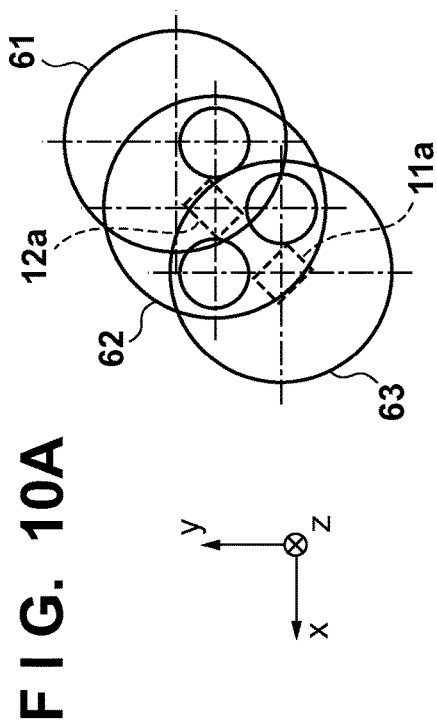
FIGS. 10A and 10B are views exemplifying the positional relationship between lenses on the x-y plane of the adaptive optical apparatus according to the fifth embodiment.
Figure 10B:
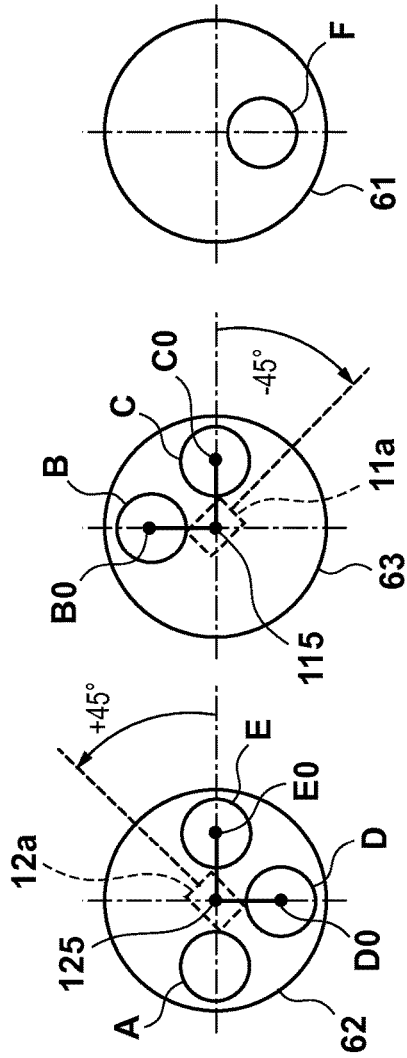

FIGS. 8, 9, 10A, and 10B show an arrangement according to the fifth embodiment of the present invention. FIG. 8 shows the x-z section of an adaptive optics SLO 105 (adaptive optical apparatus) according to the fifth embodiment, and FIG. 9 shows the y-z section. FIGS. 10A and 10B are views exemplifying the positional relationship between lenses 61, 62, and 63 on the x-y plane. Here, only an optical system from an optical fiber 9 to a reflection scanner 31 will be explained. The numerals of respective elements comply with those in the first to fourth embodiments. The adaptive optics SLO 105 according to the fifth embodiment uses, as a wavefront corrector, a reflection spatial phase modulator (liquid crystal SLM (Spatial Light Modulator): to be referred to as a "liquid crystal SLM" hereinafter). The liquid crystal can correct only a polarized component of light in a specific direction. To efficiently correct polarized components, two liquid crystal SLMs are used to correct a vertically polarized component (first component of the wavefront aberration) and a horizontally polarized component (second component of the wavefront aberration) as polarized components. A liquid crystal SLM 11a to be described below corresponds to the first wavefront corrector 11 described in the above embodiment, and a liquid crystal SLM 12a corresponds to the second wavefront corrector 12 described in the above embodiment.

According to the present invention, light does not pass through the optical axis of a lens or mirror. When, therefore, light passes through a lens or is reflected by a mirror, astigmatism aberration occurs. By shifting the facing lenses 61 to 63 with respect to the optical axis in the x-y plane, the generated astigmatism aberration is canceled and reduced.

In FIG. 8, light (for example, a wavelength of 840 nm) propagating through the optical fiber 9 from a light source (not shown) emerges as divergent light from the end face of the optical fiber 9, and is collimated by a collimator lens 8. The collimated light passes through two beam splitters 121a and 121b, and is reflected by a mirror 71. The beam diameter at this time is, for example, 6 mm. After passing through the lenses 62 and 63, the light enters the liquid crystal SLM 11a and is reflected by it. The light reflected by the liquid crystal SLM 11a passes through the lenses 63 and 62, and then enters the liquid crystal SLM 12a. In this case, the lenses 62 and 63 have the same focal distance (for example, 150 mm). The diameter of the beam entering the liquid crystal SLMs 11a and 12a is 6 mm, which is equal to the diameter of the beam reflected by the mirror 71. After the light reflected by the liquid crystal SLM 12a passes through the lens 62 and then the lens 61, it is reflected by a mirror 72. The light reflected by the mirror 72 enters the reflection scanner 31 and is scanned. At this time, the focal distance of the lens 61 is, for example, 75 mm, which is ½ of the focal distance (=150 mm) of the lenses 62 and 63. The beam diameter of the light entering the reflection scanner 31 is 3 mm.

Light entering an eye to be examined via a scanning optical system (not shown) is scanned on the retina. Return light which has been reflected and backscattered by the retina propagates through a reverse optical path. After the return light propagating through the reverse optical path is reflected by the mirror 71, part of the light is reflected by the beam splitter 121b and enters a wavefront detector 2. Information about the wavefront of the eye to be examined that has been detected by the wavefront detector 2 is sent to an information processing unit 90. The information processing unit 90 calculates a wavefront aberration based on the wavefront information acquired from the wavefront detector 2, and performs modulation driving of the two liquid crystal SLMs 11a and 12a to cancel the wavefront aberration. The return light from the eye to be examined for which the aberration has been corrected satisfactorily is reflected by the beam splitter 121a, passes through a pinhole 25, is detected by a photodetector 20, and converted into an electrical signal. The converted electrical signal is sent to the information processing unit 90, and the information processing unit 90 forms a two-dimensional image.

FIGS. 10A and 10B are views showing the x-y planes of the lenses 61, 62, and 63. As shown in FIG. 10A, the optical axis of the lens 63 is shifted by, for example, about 9 mm respectively in the +x and −y directions with respect to the optical axis of the lens 62. Also, the optical axis of the lens 61 is shifted by, for example, about 9 mm in the −x direction and about 5.3 mm in the +y direction with respect to the optical axis of the lens 62 (FIG. 10A). The shift amount (lens eccentric amount) depends on the refractive power (optical power) of the lens. For example, as the refractive power (optical power) of the lens becomes larger, the eccentric amount becomes smaller. Light passing through each lens first passes through a portion A of the lens 62 in FIG. 10B and then a portion B of the lens 63. After reflected by the liquid crystal SLM 11a, the light passes through a portion C of the lens 63 and then a portion D of the lens 62. After the light is reflected by the liquid crystal SLM 12a and passes through a portion E of the lens 62, it passes through a portion F of the lens 61, is reflected by the mirror 72, and enters the reflection scanner 31.

With this arrangement, an astigmatism aberration generated by one lens is canceled by an astigmatism aberration generated by another lens and is reduced. As a result, the imaging relationship between the wavefront detector 2, the two liquid crystal SLMs 11a and 12a, and the second reflection scanner 31, and the wavefront of light entering the reflection scanner 31 can ensure satisfactory states. Since light enters the three lenses with eccentricity with respect to their optical axes, light reflected by the lens surface does not return to the original optical path. Thus, the light reflected by the lens surface is not detected as a noise signal by the wavefront detector 2. The wavefront detector 2 can detect preferable information about the wavefront of an eye to be examined, free from any noise signal.

When the liquid crystal SLM is used, attention needs to be paid to the polarization state of incident light. The liquid crystal SLM can perform a phase modulation action for only a polarized component in a specific direction owing to the characteristic of the liquid crystal. To prevent the influence on the polarization state when only phase modulation is performed, a beam in the P-polarized state needs to enter the liquid crystal SLM. In the fifth embodiment, as for the liquid crystal SLM 11a, an incident beam enters a center 115 of the liquid crystal SLM 11a from a position BO of a principal ray on the lens 63, is reflected at the center 115 of the liquid crystal SLM 11a, and traces an optical path extending to a position C0 of the principal ray on the lens 63. A plane including these three points serves as an incident surface. To satisfy the P-polarization condition, a beam polarization direction of −45° (counterclockwise direction in the +z direction is defined as a positive direction) with respect to the x-y plane needs to coincide with the modulation action direction of the liquid crystal SLM 11a. To achieve this, the reflection surface of the liquid crystal SLM 11a is also arranged to be inclined by −45°.

This also applies to the liquid crystal SLM 12a. An incident beam enters a center 125 of the liquid crystal SLM 12a from a position D0 of a principal ray on the lens 62, is reflected at the center 125 of the liquid crystal SLM 12a, and traces an optical path extending to a position E0 of the principal ray on the lens 62. A plane including these three points serves as an incident surface. To satisfy the P-polarization condition, a beam polarization direction of +45° with respect to the x-y plane needs to coincide with the modulation action direction of the liquid crystal SLM 12a. Therefore, the reflection surface of the liquid crystal SLM 12a is also arranged to be inclined by +45°.

With this arrangement, the wavefront aberration of an eye to be examined can be precisely measured by the optical system in which astigmatism aberration is reduced. Satisfactory wavefront correction can be performed, and the liquid crystal SLM can be used in an ideal state. FIG. 14 is a table exemplifying optical data of the adaptive optical apparatus according to the fifth embodiment. The center of plane 1 is defined as the origin of the coordinates. XSC, YSC, and ZSC are the x-, y-, and z-coordinates (unit: mm) of each plane vertex. ASC, BSC, and CSC are rotation angles (unit: °) about the x-, y-, and z-axes serving as rotation centers. REF represents the reflection surface. Glass material symbols defined by SCHOTT are used.

Figure 11:
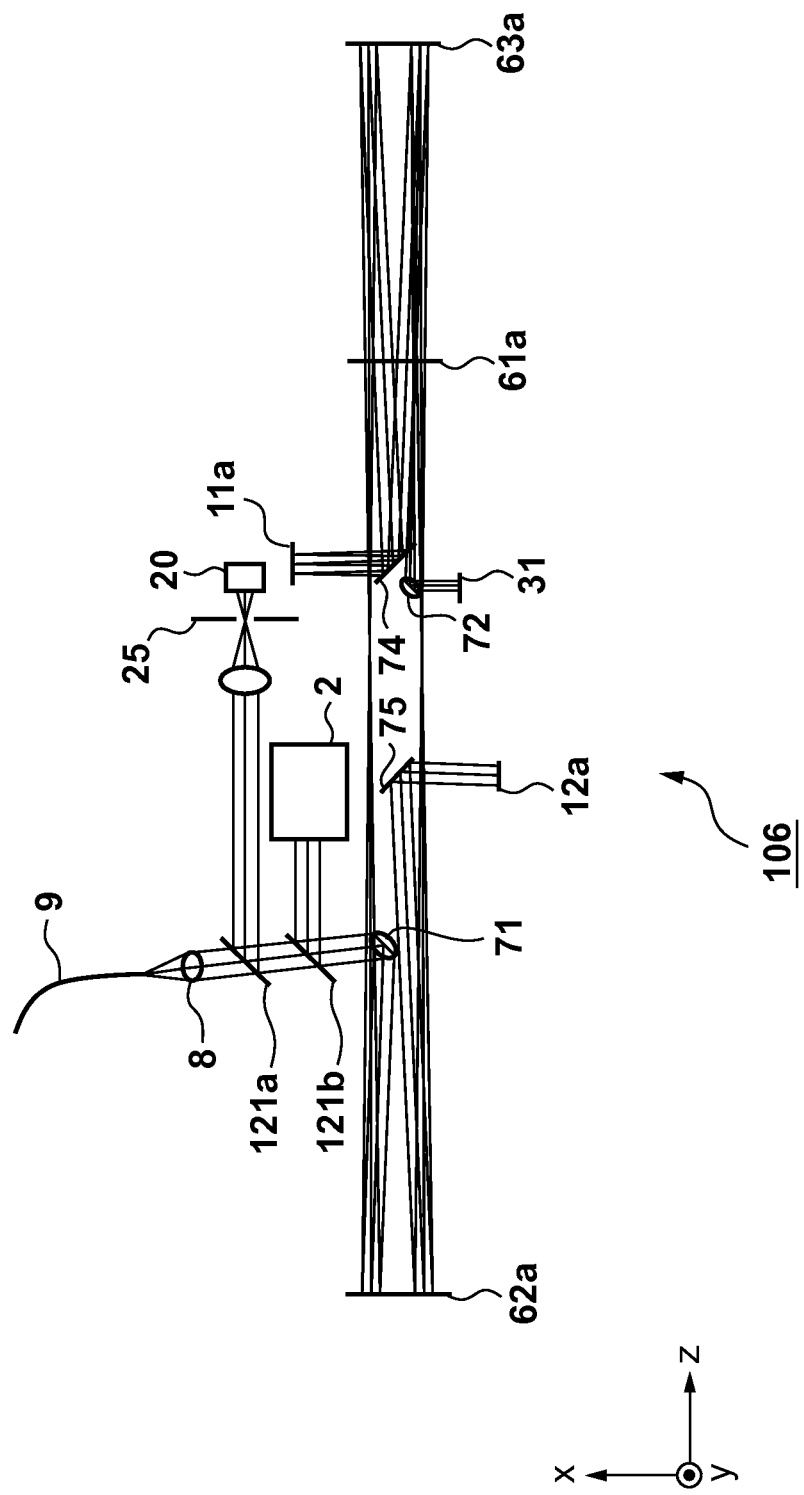
FIG. 11 is a view showing the x-z section of an adaptive optical apparatus according to the sixth embodiment.
Figure 12:
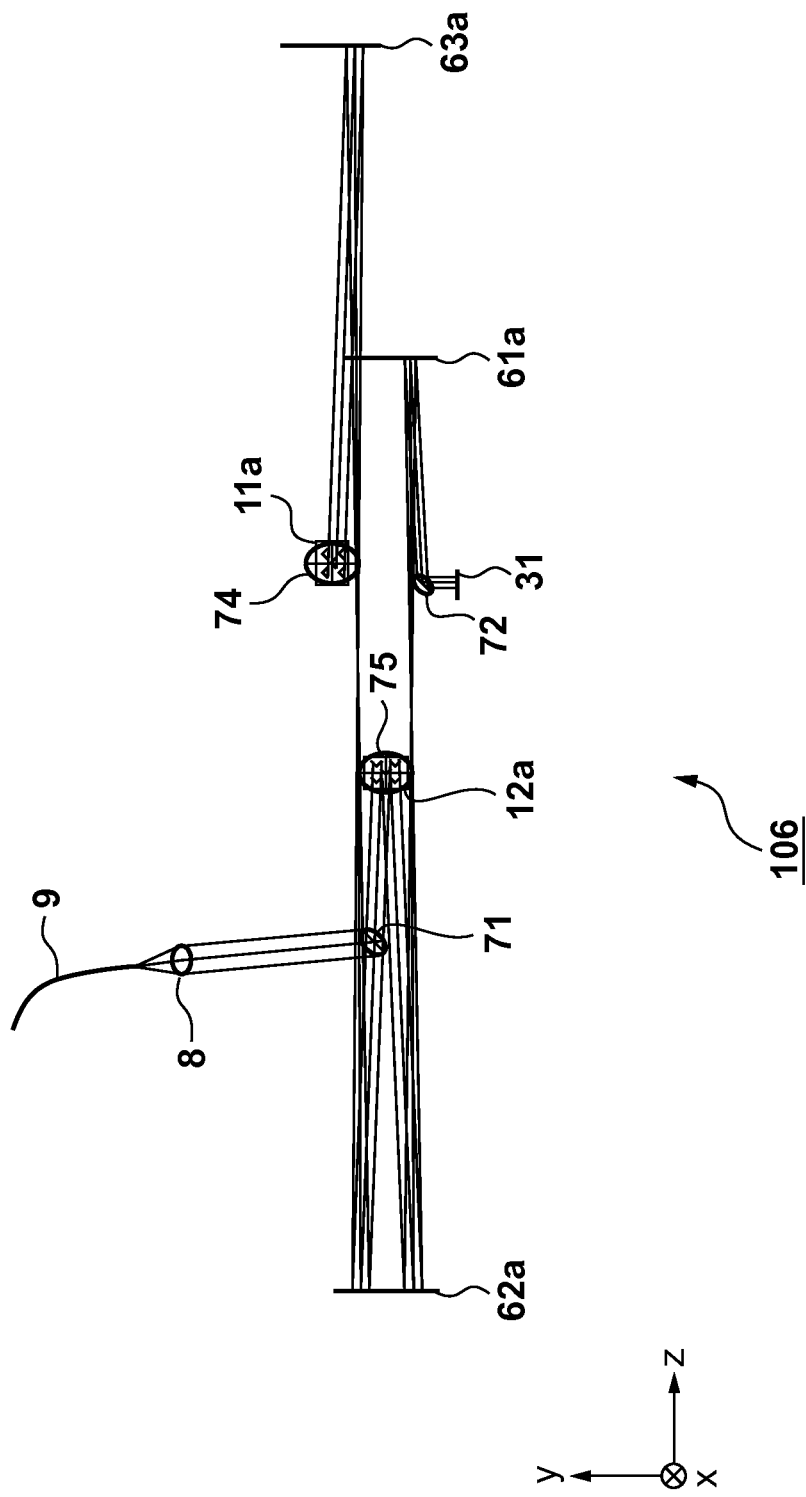
FIG. 12 is a view showing the y-z section of the adaptive optical apparatus according to the sixth embodiment.

Sixth Embodiment: Arrangement Using Concave Mirror Instead of Lens in Fifth Embodiment FIGS. 11 and 12 show an arrangement according to the sixth embodiment of the present invention. FIG. 11 shows the x-z section of an adaptive optics SLO 106 (adaptive optical apparatus) according to the sixth embodiment, and FIG. 12 shows the y-z section. In the sixth embodiment, the optical arrangement including the focal distance and the like is basically the same as that in the fifth embodiment, and the same reference numerals denote the same parts. The sixth embodiment adopts a concave mirror, instead of a lens in the fifth embodiment. In the lens system, the distance from a liquid crystal SLM 11a to a liquid crystal SLM 12a is four times larger than the focal distance of the lens. In the mirror system, however, light is deflected by a concave mirror, so the whole space can be further reduced.

Figure 13:
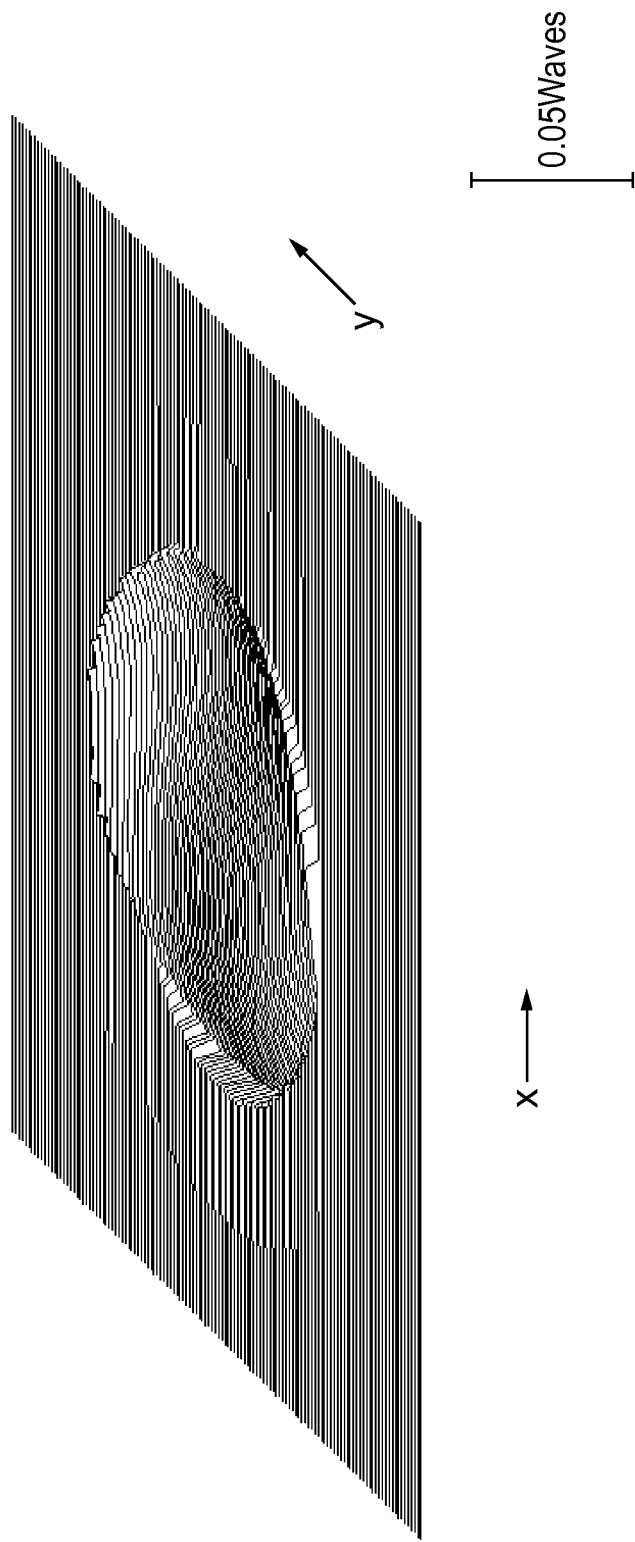
FIG. 13 is a view exemplifying the wavefront aberration of light entering a reflection scanner.

In FIG. 11, light (for example, a wavelength of 840 nm) propagating through an optical fiber 9 from a light source (not shown) emerges as divergent light from the end face of the optical fiber 9, and is collimated by a collimator lens 8. The collimated light passes through two beam splitters 121a and 121b, and is reflected by a mirror 71. The light reflected by the mirror 71 enters a concave mirror 62a. The light reflected by the concave mirror 62a enters a concave mirror 63a. The light reflected by the concave mirror 63a is deflected by a mirror 74 and enters the liquid crystal SLM 11a. The light reflected by the liquid crystal SLM 11a is deflected again by the mirror 74. The light deflected (reflected) by the mirror 74 enters the concave mirror 63a again. The light reflected by the concave mirror 63a enters the concave mirror 62a and is reflected by the concave mirror 62a. The light reflected by the concave mirror 62a is deflected (reflected) by a mirror 75 and enters the liquid crystal SLM 12a. The light reflected by the liquid crystal SLM 12a enters again a reflection scanner 31 via the mirror 75, the concave mirror 62a, a concave mirror 61a, and the mirror 72. At this time, the concave mirrors 61a to 63a are arranged at eccentric positions with respect to the optical axis, as shown in FIGS. 10A, and 10B, similar to the fifth embodiment, and can cancel astigmatism aberrations generated by them. FIG. 13 is a view exemplifying the wavefront aberration of light entering the reflection scanner 31. The RMS of the wavefront aberration is suppressed to 0.009λ.

In FIG. 11, the liquid crystal SLM 12a modulates a vertically polarized component (first component of the wavefront aberration) perpendicular to the paper surface. The liquid crystal SLM 11a modulates a horizontally polarized component (second component of the wavefront aberration) parallel to the paper surface. For this purpose, the respective liquid crystal SLMs are arranged to make their modulation action directions parallel to these polarized components.

Light entering an eye to be examined via a scanning optical system (not shown) is scanned on the retina. Return light which has been reflected and backscattered by the retina propagates through a reverse optical path. After the return light propagating through the reverse optical path is reflected by the mirror 71, part of the light is reflected by the beam splitter 121b and enters a wavefront detector 2. As described with reference to FIG. 8, information about the wavefront of the eye to be examined that has been detected by the wavefront detector 2 is sent to an information processing unit 90. The information processing unit 90 calculates a wavefront aberration based on the wavefront information acquired from the wavefront detector 2, and performs modulation driving of the two liquid crystal SLMs 11a and 12a to cancel the wavefront aberration. The return light from the eye to be examined for which the aberration has been corrected satisfactorily is reflected by the beam splitter 121a, passes through a pinhole 25, is detected by a photodetector 20, and converted into an electrical signal. As described with reference to FIG. 8, the converted electrical signal is sent to the information processing unit 90, and the information processing unit 90 forms a two-dimensional image.

FIG. 15 is a table exemplifying optical data of the adaptive optical apparatus according to the sixth embodiment. The settings of the symbols and coordinates are the same as those in the fifth embodiment. The center of plane 1 is defined as the origin. XSC, YSC, and ZSC are the x-, y-, and z-coordinates (unit: mm) of each plane vertex. ASC, BSC, and CSC are rotation angles (unit: °) about the x-, y-, and z-axes serving as rotation centers. REF represents the reflection surface. Glass material symbols defined by SCHOTT are used.

According to the sixth embodiment, the size of the optical system is suppressed to an area of about 300 mm×100 mm, and the optical system can be downsized to a fraction of a conventional adaptive optical system.

The adaptive optical apparatus described in each of the embodiments is applicable not only to an ophthalmic apparatus but also to an endoscope apparatus. In this case, the endoscope apparatus suffices to include a light source, an adaptive optical apparatus, and an unit for arranging the adaptive optical apparatus into the body (body cavity).

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-247747, filed Nov. 9, 2012, which is hereby incorporated by reference herein in its entirety.

The invention claimed is:

1. An adaptive optical apparatus comprising:
    a wavefront detection unit configured to detect a wavefront aberration;
    a wavefront correction unit configured to correct the wavefront aberration;
    a first scanning unit, arranged to be optically substantially conjugate to said wavefront correction unit, configured to scan measurement light from a light source on an object in a first direction;
    a second scanning unit, arranged to be optically substantially conjugate to said wavefront correction unit, configured to scan light on the object in a second direction; and
    an optical element commonly arranged (a) in a first optical path between said wavefront correction unit and said first scanning unit, (b) in a second optical path between said first scanning unit and said second scanning unit, and (c) in a third optical path between said wavefront detection unit and said wavefront correction unit, the first optical path, the second optical path, and the third optical path being different from each other,
    wherein said wavefront correction unit reflects light from the light source, and the light reflected by said wavefront correction unit irradiates said first scanning unit via a first region of said optical element,
    wherein the light reflected by said first scanning unit irradiates said second scanning unit via a second region of said optical element, and
    wherein said wavefront correction unit reflects light reflected by the object, and the light reflected by said wavefront correction unit irradiates said wavefront detection unit via a third region of said optical element.

2. The apparatus according to claim 1, wherein the first region and the third region are end regions on a surface of said optical element, and
    wherein the second region is a region at a center positioned between the end regions on the surface of said optical element.

3. The apparatus according to claim 1, further comprising a second optical element arranged in an optical path between said second scanning unit and the object,
    wherein measurement light scanned by said second scanning unit irradiates the object via a first region of said second optical element, and
    wherein the return light from the object irradiates said second scanning unit via a second region of said second optical element that is different from the first region.

4. An adaptive optical apparatus comprising:
    a wavefront detection unit configured to detect a wavefront aberration;
    a first wavefront correction unit configured to correct a first component of the wavefront aberration;
    a second wavefront correction unit, arranged to be optically substantially conjugate to said first wavefront correction unit, configured to correct a second component of the wavefront aberration that is different from the first component;

a first scanning unit, arranged to be optically substantially conjugate to said first wavefront correction unit and said second wavefront correction unit, configured to scan measurement light from a light source on an object in a first direction; and an optical element commonly arranged (a) in a first optical path between said first wavefront correction unit and said second wavefront correction unit, (b) in a second optical path between said second wavefront correction unit and said first scanning unit, and (c) in a third optical path between said wavefront detection unit and said first wavefront correction unit, the first optical path, the second optical path, and the third optical path being different from each other, wherein the measurement light irradiates said first wavefront correction unit via a first region of said optical element, wherein the measurement light reflected by said first wavefront correction unit irradiates said second wavefront correction unit via a second region of said optical element, and wherein the measurement light reflected by said second wavefront correction unit irradiates said scanning unit via a third region of said optical element.

5. The apparatus according to claim 4, wherein the third region is a region at a center on a surface of said optical element, wherein the first region and the second region are end regions at different positions on the surface of said optical element, and wherein the region at the center is positioned between the end regions at the different positions.

6. The apparatus according to claim 4, further comprising:

a second scanning unit configured to scan the measurement light on the object in a second direction perpendicular to the first direction; and a second optical element arranged in an optical path between said second scanning unit and the object, wherein the measurement light scanned by said first scanning unit irradiates said second scanning unit via a first region of said second optical element, wherein said second scanning unit scans, in the second direction, the measurement light scanned in the first direction by said scanning unit, and the measurement light scanned by said second scanning unit irradiates the object via a second region of said second optical element that is different from the first region, and wherein the return light from the object irradiates said second scanning unit via the second region of said second optical element.

7. The apparatus according to claim 6, wherein an area of the second region on a surface of said second optical element is larger than an area of the first region of said second optical element.

8. The apparatus according to claim 1, wherein said optical element includes one of a lens and a mirror.

9. A method of controlling an adaptive optical apparatus comprising (1) a wavefront detection unit configured to detect a wavefront aberration, (2) a wavefront correction unit configured to correct the wavefront aberration, (3) a first scanning unit, arranged to be optically substantially conjugate to the wavefront correction unit, configured to scan measurement light from a light source on an object in a first direction, (4) a second scanning unit, arranged to be optically substantially conjugate to the wavefront correction unit, configured to scan light on the object in a second direction, and (5) an optical element commonly arranged (a) in a first optical path between the wavefront correction unit and the first scanning unit, (b) in a second optical path between the first scanning unit and the second scanning unit, and (c) in a third optical path between the wavefront detection unit and the wavefront correction unit, the first optical path, the second optical path, and the third optical path being different from each other, wherein the wavefront correction unit reflects light from the light source, and the light reflected by the wavefront correction unit irradiates the first scanning unit via a first region of the optical element, wherein the light reflected by the first scanning unit irradiates the second scanning unit via a second region of the optical element, and wherein the wavefront correction unit reflects light reflected by the object, and the light reflected by the wavefront correction unit irradiates the wavefront detection unit via a third region of the optical element, the method comprising a generation step of generating an image of an eye to be examined for which a wavefront aberration is corrected by the adaptive optical apparatus.

10. An ophthalmic apparatus comprising:

an adaptive optical apparatus comprising (1) a wavefront detection unit configured to detect a wavefront aberration, (2) a wavefront correction unit configured to correct the wavefront aberration, (3) a first scanning unit, arranged to be optically substantially conjugate to said wavefront correction unit, configured to scan measurement light from a light source on an object in a first direction, (4) a second scanning unit, arranged to be optically substantially conjugate to said wavefront correction unit, configured to scan light on the object in a second direction, and (5) an optical element commonly arranged (a) in a first optical path between said wavefront correction unit and said first scanning unit, (b) in a second optical path between said first scanning unit and said second scanning unit, and (c) in a third optical path between said wavefront detection unit and said wavefront correction unit, the first optical path, the second optical path, and the third optical path being different from each other, wherein said wavefront correction unit reflects light from the light source, and the light reflected by said wavefront correction unit irradiates said first scanning unit via a first region of said optical element, wherein the light reflected by said first scanning unit irradiates said second scanning unit via a second region of said optical element, and wherein said wavefront correction unit reflects light reflected by the object, and the light reflected by said wavefront correction unit irradiates said wavefront detection unit via a third region of said optical element, wherein the object includes an eye to be examined; and a generation unit configured to generate an image of the eye to be examined for which a wavefront aberration is corrected by said adaptive optical apparatus.

11. A method of controlling an adaptive optical apparatus comprising (1) a wavefront detection unit configured to detect a wavefront aberration, (2) a first wavefront correction unit configured to correct a first component of the wavefront aberration, (3) a second wavefront correction unit, arranged to be optically substantially conjugate to the first wavefront correction unit, configured to correct a second component of the wavefront aberration that is different from the first component, (4) a first scanning unit, arranged to be optically substantially conjugate to the first wavefront correction unit and the second wavefront correction unit, configured to scan measurement light from a light source on an object in a first direction, and (5) an optical element commonly arranged (a) in a first optical path between the first wavefront correction unit and the second wavefront correction unit, (b) in a second optical path between the second wavefront correction unit and the first scanning unit, and (c) in a third optical path between the wavefront detection unit and the first wavefront correction unit, the first optical path, the second optical path, and the third optical path being different from each other, wherein the measurement light irradiates the first wavefront correction unit via a first region of the optical element, wherein the measurement light reflected by the first wavefront correction unit irradiates the second wavefront correction unit via a second region of the optical element, and wherein the measurement light reflected by the second wavefront correction unit irradiates the scanning unit via a third region of the optical element, the method comprising a generation step of generating an image of an eye to be examined for which a wavefront aberration is corrected by the adaptive optical apparatus.

12. An ophthalmic apparatus comprising:
an adaptive optical apparatus comprising (1) a wavefront detection unit configured to detect a wavefront aberration, (2) a first wavefront correction unit configured to correct a first component of the wavefront aberration, (3) a second wavefront correction unit, arranged to be optically substantially conjugate to said first wavefront correction unit, configured to correct a second component of the wavefront aberration that is different from the first component, (4) a first scanning unit, arranged to be optically substantially conjugate to said first wavefront correction unit and said second wavefront correction unit, configured to scan measurement light from a light source on an object in a first direction, and (5) an optical element commonly arranged (a) in a first optical path between said first wavefront correction unit and said second wavefront correction unit, (b) in a second optical path between said second wavefront correction unit and said first scanning unit, and (c) in a third optical path between said wavefront detection unit and said first wavefront correction unit, the first optical path, the second optical path, and the third optical path being different from each other, wherein the measurement light irradiates said first wavefront correction unit via a first region of said optical element, wherein the measurement light reflected by said first wavefront correction unit irradiates said second wavefront correction unit via a second region of said optical element, and wherein the measurement light reflected by said second wavefront correction unit irradiates said scanning unit via a third region of said optical element, wherein the object includes an eye to be examined; and
a generation unit configured to generate an image of the eye to be examined for which a wavefront aberration is corrected by said adaptive optical apparatus.

* * * * *